United States Patent [19]

Gsell

[11] Patent Number: 4,963,572
[45] Date of Patent: * Oct. 16, 1990

[54] N-PYRIDYL METHYL-N-'-CYANOISOTHIOUREA COMPOUNDS USEFUL IN CONTROLLING INSECT PESTS

[75] Inventor: Laurenz Gsell, Basel, Switzerland

[73] Assignee: Ciba-Geigy Corporation, Ardsley, N.Y.

[ * ] Notice: The portion of the term of this patent subsequent to Oct. 16, 2007 has been disclaimed.

[21] Appl. No.: 229,209

[22] Filed: Aug. 8, 1988

[30] Foreign Application Priority Data

Aug. 12, 1987 [CH] Switzerland .......................... 3099/87

[51] Int. Cl.$^5$ .............................................. A61K 31/44
[52] U.S. Cl. ...................................... 514/357; 546/330
[58] Field of Search .......................... 546/330; 514/357

[56] References Cited

FOREIGN PATENT DOCUMENTS 6176044 2/1986 Japan .................................... 546/330

OTHER PUBLICATIONS

Chemical Abstracts, vol. 90, No. 11, Abstract No. 87,289f, Mar. 12, 1979, p. 608, Hirata et al.
Hackh's Chemical Dictionary–Fourth Edition (1969).

*Primary Examiner*—Mary C. Lee
*Assistant Examiner*—Zinna Northington Davis
*Attorney, Agent, or Firm*—Kevin T. Mansfield; Edward McC.Roberts

[57] ABSTRACT

Novel substituted N-pyridylmethyl-N'-cyanoisothioureas of formula

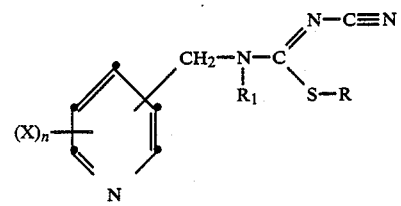

wherein R is $C_1$-$C_4$alkyl, cyclopropyl or benzyl; $R_1$ is $C_1$-$C_4$alkyl or cyclopropyl; X is halogen; and n is the integer 0, 1, 2 or 3.

Processes for the preparation of these compounds, the corresponding starting materials and intermediates and the use of the novel compounds in pest control, especially for controlling insects and representatives of the order Acarina, especially insect pests in rice crops, and as starting materials for the synthesis of novel pesticidal compositions are described.

10 Claims, No Drawings

N-PYRIDYL METHYL-N-'-CYANOISOTHIOUREA COMPOUNDS USEFUL IN CONTROLLING INSECT PESTS

The present invention relates to novel substituted N-pyridylmethyl-N'-cyanoisothioureas, to processes for the preparation thereof and to their use in pest control and as starting materials for the synthesis of novel pesticidal compositions.

The invention relates to novel compounds of formula I

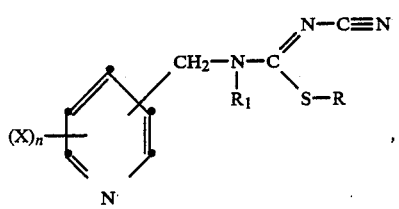

wherein R is $C_1$-$C_4$alkyl, cyclopropyl or benzyl; $R_1$ is $C_1$-$C_4$alkyl or cyclopropyl; X is halogen; and n is the integer 0, 1, 2 or 3.

Preferred according to the invention are compounds of formula I wherein R is methyl, ethyl or benzyl; $R_1$ is methyl; X is chlorine; and n is the integer 0, 1 or 2.

Also preferred according to the invention are compounds of formula I wherein R and $R_1$ are methyl; and n is the integer 0.

Of particular interest are those compounds of formula I according to the invention wherein the pyridyl radical is a pyrid-3yl or pyrid-4-yl radical.

"Alkyl", as an independent radical or as part of another substituent, shall be understood as meaning a straight-chain or branched alkyl group and, depending on the number of carbon atoms indicated, within the scope of the present invention is, for example, one of the following groups: methyl, ethyl, propyl, butyl, and the isomers thereof, such as isopropyl, isobutyl, tert.-butyl and sec.-butyl.

The term "halogen" within the scope of the present invention is to be understood as meaning fluorine, chlorine and bromine, preferably fluorine and chlorine.

The present invention also relates to the salts, especially the phytophysiologically tolerable salts, of the compounds of formula I. The following are examples of suitable salts of this kind with organic and inorganic acids: chlorides, bromides, iodides, sulfates, hydrogen sulfates, chlorates, perchlorates, thiocyanates, nitrates, phosphates, hydrogen phosphates, tetrafluoroborates, formates, acetates, trichloroacetates, trifluoroacetates, phenylsulfonates, oxalates, malonates, succinates, malates, tartrates and citrates.

The compounds of formula I can be prepared in a manner known per se (see, for example, JP Pat. application Kodai No. 62-234064; J. P. Hendrickson et al., "Organic Chemistry", McGraw Hill Book Co., 1970, pages 378-382) by reacting a compound of formula II

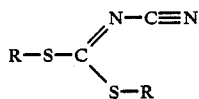

with a compound of formula III

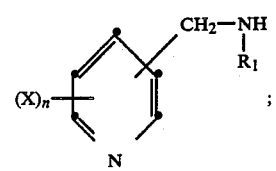

R, $R_1$, X and n in formulae II and III being as defined above. In this reaction, one of the radicals —S—R is a leaving group that can be removed under the reaction conditions.

The above process variants resulting in the compounds of formula I according to the invention are preferably carried out in a solvent. Suitable solvents are, for example, aromatic hydrocarbons, such as benzene, toluene and xylene; ketones, such as acetone, cyclohexanone and methyl ethyl ketone; ethers, such as tetrahydrofuran, dioxan and diethyl ether; halogenated hydrocarbons, such as chloroform, carbon tetrachloride and chlorobenzene; alcohols, such as ethanol and propanol; esters of aliphatic acids, such as ethyl acetate; aliphatic amides, such as dimethylformamide and dimethylacetamide; dimethyl sulfoxide, acetonitrile and other solvents that do not impair the reaction. These solvents can also be used in the form of mixtures. The reaction temperature may be in a wide range of from −10 to +150 ° C. A temperature range of approximately from 20° to 80° C. is preferred.

The starting compounds of formulae II and III are known or, if novel, can be obtained analogously to known methods. For example, N-cyanothioiminocarbonates of formula II, and the preparation thereof, are known from Chem. Ber. 100, 2604–15 (1967); J. Hetero. Chem. 19, 1205–6 (1982), and JP Pat. application SHO 61-76044. The picolylamine compounds of formula III are also known or can be obtained analogously to, for example, Tetrahedron Letters Vol. 26, 5863 (1985) or Agr. Biol. Chem. 32, 747 (1968).

N-picolyl-N'-cyanoisothioureas, their preparation and their use as pharmaceuticals have already been described in JP Pat. application SHO 61-76044. The compounds of formula I according to the invention differ structurally from those compounds by the alkyl substitution at the N atom ($R_1$ in formula I).

Surprisingly, it has now been found that the compounds of formula I according to the invention have excellent pesticidal activity while being well tolerated by plants and having low toxicity to warm-blooded animals. They are suitable especially for controlling pests that attack plants and animals.

The compounds of formula I are especially suitable for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and representatives of the order Acarina.

The good pesticidal activity of the compounds according to the invention corresponds to a mortality of at least from 50 to 60% of the pests mentioned.

Using the compounds of formula I according to the invention it is possible to control especially plant-destructive insects, especially plant-destructive insects in crops of ornamental and useful plants, especially cotton crops, vegetable crops, rice crops and fruit crops. In this connection, attention is drawn to the fact that the said compounds are distinguished by a very pronounced systemic action, especially by contact action, against sucking insects, especially against insects of the Aphididae family (such as, for example, Aphis fabae, Aphis craccivora and Myzus persicae), that can be controlled by conventional pesticides only with difficulty.

The compounds of formula I are also distinguished by a good action against larval insect stages and against nymphs, especially of feeding insect pests. In particular, the compounds of formula I can be used with outstanding success against plant-destructive cicadas, especially in rice crops. In this connection attention is drawn to the low toxicity to fish of the compounds according to the invention.

The compounds are also suitable for controlling ectoparasites, for example Lucilia sericata, and ticks on domestic animals and productive livestock, for example by treating the animals, livestock buildings and pastures.

The activity of the compounds according to the invention and of compositions containing them can be substantially broadened and adapted to prevailing circumstances by adding other insecticides and/or acaricides. Suitable additives are, for example, representatives of the following classes of active ingredient: organophosphorus compounds, nitrophenols and derivatives thereof, formamidines, ureas, carbamates, pyrethroids, chlorinated hydrocarbons and Bacillus thuringiensis preparations.

The compounds of formula I are used in unmodified form or, preferably, together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) or combinations thereof with other insecticides or acaricides and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Depending on the nature of the compound of formula I to be formulated, or on the nature of the combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Other suitable surfactants that may be mentioned are fatty acid methyltaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$—$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in the art of formulation are described, inter alia, in the following publications:

"Mc Cutcheon's Detergents and Emulsifiers Annual" MC Publishing Corp., Ridgewood, NJ, 1979;

Dr. Helmut Stache "Tensid Taschenbuch", Carl Hanser Verlag,
Munich/Vienna 1981.

The pesticidal compositions usually contain—based on weight —0.1 to 99%, preferably 0.1 to 95%, of a compound of formula I or combinations thereof with other insecticides or acaricides, 1 to 99.9% of a solid or liquid adjuvant, and 0 to 25%, preferably 0.1 to 20%, of a surfactant. Whereas commercial products will preferably be formulated as concentrates, the end user will normally employ dilute formulations containing substantially lower concentrations of active ingredient, for example from 0.1 to 1000 ppm.

The compositions may also contain further additives such as stabilisers, antifoams, viscosity regulatiors, binders and tackifiers as well as fertilisers or other active ingredients for obtaining special effects.

The isothiourea compounds of formula I according to the invention are also suitable for use as starting materials or intermediates for the preparation of pesticidally, especially insecticidally, active guanidine compounds. The present invention therefore also relates to the use of a compound of formula I for the preparation of pesticidally active guanidine compounds of formula IV and tautomers thereof $$(IV)$$

wherein each of $R_1$ and $R_2$, independently of the other, is $C_1$—$C_4$alkyl, $R_3$ is hydrogen, $C_1$—$C_4$alkyl, benzyl or picolyl; or $R_2$ and $R_3$ together are a radical $-(CH_2)_4-$ or $-(CH_2)_5-$; X is halogen; and n is the integer 0, 1, 2 or 3; by reacting a compound of formula I with a compound of formula V $$H-N\begin{matrix}R_2\\R_3\end{matrix} \qquad (V)$$

wherein $R_2$ and $R_3$ are as defined above.

EXAMPLE 1

PREPARATION OF N-PYRID-3-3-YLMETHYL-N-METHYL-N'-CYANO-S-METHYL-ISOTHIOUREA 5.1 g of dimethyl-N-cyanothioiminocarbonate, 4.3 g of 3-methylamino-methylpyridine and 10.6 g of ammonium acetate in 20 ml of ethanol are refluxed for 8 hours. When the reaction mixture has cooled, the salts are removed and the solvents are distilled off. After purification by chromatography, the product is isolated in the form of a pale oil. In this manner the title compound of formula having a refraction of $n_D^{20}$'''1.6098 (compound no. 1) is obtained.

The following compounds of formula I are also prepared as indicated above:

| comp. no. | pyridyl position | R | $R_1$ | X | n | phys. data |
|---|---|---|---|---|---|---|
| 2 | 4- | ▷ | H | — | 0 | m.p. = 125–26° C. |
| 3 | 3- | —$C_3H_7(i)$ | H | — | 0 | m.p. = 107–109,5° C. |
| 4 | 4- | —$CH_3$ | —$C_3H_7(n)$ | — | 0 | $n_D^{23}$ = 1,5951 |
| 5 | 3- | —$CH_3$ | ▷ | — | 0 | $n_D^{24}$ = 1,6105 |

The following compounds of formula I can also be obtained as indicated above:

| pyridyl position | R | $R_1$ | X | n |
|---|---|---|---|---|
| 3- | —$CH_3$ | —$C_2H_5$ | — | 0 |
| 3- | —$CH_3$ | —$C_4H_9(n)$ | — | 0 |
| 2- | —$CH_3$ | —$CH_3$ | — | 0 |
| 2- | —$CH_3$ | —$C_2H_5$ | — | 0 |
| 4- | —$CH_3$ | —$CH_3$ | — | 0 |
| 4- | —$CH_3$ | —$C_4H_9(n)$ | — | 0 |

EXAMPLE 2

PREPARATION OF N-PYRID-3-YLMETHYL-N-METHYL-N'-CYANO-N"-N-BUTYLGUANIDINE 4.5 g of compound no. 1 prepared according to Example 1, together with 2 ml of n-butylamine and 20 ml of ethanol, are refluxed for 16 hours. After distilling off the volatile portions in a rotary evaporator, the residue is purified by chromatography on a silica gel column while eluting with dichloromethane/methanol (90/10% by volume). The title compound of formula

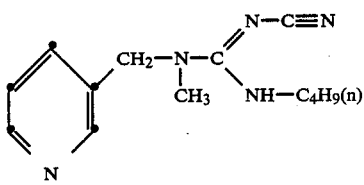

is obtained in the form of a pale yellow oil ($n_D^{22} = 1.5598$).

EXAMPLE 3

Formulations for Liquid Active Ingredients of Formula I according to Example 1 or Combinations of these Active Ingredients with other Insecticides or Acaricides (Throughout, Percentages are by Weight)

| 3.1. Emulsifiable concentrates | (a) | (b) | (c) |
|---|---|---|---|
| active ingredient or combination | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 3.2. Solutions | (a) | (b) | (c) | (d) |
|---|---|---|---|---|
| active ingredient or combination | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

These solutions are suitable for application in the form of micro-drops.

| 3.3. Granulates | (a) | (b) |
|---|---|---|
| active ingredient or combination | 5% | 10% |
| kaolin | 94% | — |
| highly dispersed silicic acid | 1% | — |
| attapulgite | — | 90% |

The active ingredient or combination is dissolved in methylene chloride, the solution is sprayed onto the carrier, and the solvent is subsequently evaporated off in vacuo.

| 3.4. Dusts | (a) | (b) |
|---|---|---|
| active ingredient or combination | 2% | 5% |
| highly dispersed silicic acid | 1% | 5% |
| talcum | 97% | — |
| kaolin | — | 90% |

Ready-for-use dusts are obtained by intimately mixing the carriers with the active ingredient or combination.

Formulations for Solid Active Ingredients of Formula I according to Example 1 or Combinations of these Active Ingredients with other Insecticides or Acaricides (Throughout, Percentages are by Weight)

| 3.5. Wettable powders | (a) | (b) | (c) |
|---|---|---|---|
| active ingredient or combination | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient or combination is thoroughly mixed with the adjuvants and the mixture is thoroughly ground in a suitable mill, affording wettable powders which can be diluted with water to give suspensions of the desired concentration.

| 3.6. Emulsifiable concentrate | |
|---|---|
| active ingredient or combination | 10% |
| octylphenol polyethylene glycol ether (4–5 moles of ethylene oxide) | 3% |
| calcium dodecylbenzenesulphonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| 3.7. Dusts | (a) | (b) |
|---|---|---|
| active ingredient or combination | 5% | 8% |
| talcum | 95% | — |
| kaolin | — | 92% |

Ready-for-use dusts are obtained by mixing the active ingredient or combination with the carrier and grinding the mixture in a suitable mill.

| 3.8. Extruder granulate | |
|---|---|
| active ingredient or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded, granulated and then dried in a stream of air.

| 3.9. Coated granulate | |
|---|---|
| active ingredient or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| 3.10. Suspension concentrate | |
|---|---|
| active ingredient or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient or combination is intimately mixed with the adjuvants, giving a suspension concentrate from which suspensions of any desired concentration can be obtained by dilution with water.

EXAMPLE 4

Insecticidal Contact Action: *Aphis Craccivora*

Before the start of the test, plants (*Vicia faba*) reared in pots are each populated with about 200 insects of the species *Aphis craccivora*. The treated plants are sprayed to drip point 24 hours later with an aqueous formulation containing 400 ppm of the test compound. Two plants are used for each test compound, and a mortality count is made after a further 24 hours.

Compounds of formula I according to Example 1 exhibit good activity (mortality) in this test.

EXAMPLE 5

Insecticidal Systemic Action: *Aphis Craccivora*

Rooted bean plants are transplanted into pots containing 600 ccm of soil. 50 ml of a formulation (prepared from a 25% wettable powder) of the test compound in a concentration of 400 ppm are then poured directly onto the soil in each pot.

After 24 hours the epigeous parts of the plants are populated with aphids of the species *Aphis craccivora* and a plastic cylinder is then slipped over the plants to protect the aphids from any possible contact with the test substance either directly or via the gas phase.

A mortality count is made 48 and 72 hours after the start of the test. Two plants, each in a separate pot, are used for each test substance. The test is carried out at 25° C. and 70% relative humidity.

The compounds of formula I according to Example 1 exhibit good activity in this test.

EXAMPLE 6

Insecticidal Contact Action: *Myzus Persicae*

Pea seedlings about 4 cm high which have been reared in water are each populated with about 200 insects of the species *Myzus persicae* before the start of the test. The treated plants are sprayed to drip point 24 hours later with an aqueous suspension containing 400 ppm of the test compound. Two plants are used for each batch. A mortality count is made 48 hours after application. The test is carried out at 20° to 22° C. and 60% relative humidity.

The compounds of formula I according to Example 1 exhibit good activity in this test.

EXAMPLE 7

Insecticidal Systemic Action: *Myzus Persicae*

Rooted cabbage plants are transplanted at the 4- to 5-leaf stage into pots containing 60 ccm of soil. 50 ml of an aqueous formulation (prepared from a 25% wettable powder) of the test compound of formula I in each case in a concentration of 400 ppm, are then poured directly onto the soil.

After 24 hours the epigeous parts of the treated plants are populated with aphids of the species *Myzus persicae* and plastic cylinders are slipped over the plants to protect the aphids from any possible contact with the test substance either directly or via the gas phase.

A mortality count is made 48 hours after the start of the test. Two plants, each in a separate pot, are used for each test substance. The test is carried out at about 25° C. and 60% relative humidity.

The compounds of formula I according to Example 1 exhibit good activity in this test.

EXAMPLE 8

Insecticidal Leaf Penetration Action: *Aphis Craccivora*

A suitably small sprig of *Vicia faba* severely infested with aphids of the species *Aphis craccivora* is placed in each of a number of plastic beakers about 8 cm in height (diameter about 6 cm). Each beaker is covered with a plastic lid having a punched opening of 2 cm diameter in the centre. A leaf of a *Vicia faba* plant is placed over the opening in the lid without separating this leaf from the potted plant. The leaf is then fixed on the beaker above the opening in the first lid with a second punched lid. From underneath, i.e. through the opening in the first lid, the aphids in the beaker then infest the overlying leaf of the plant used as bait. An aqueous formulation of the test compound is uniformly applied in a concentration of 400 ppm to the upper side of the leaf using a brush. An examination is then made to determine whether the test substance applied to the upper side of the leaf of the plant used as bait has diffused through the leaf to the underside thereof in an amount sufficient to kill the aphids sucking thereon.

The test is carried out at about 20° C. and 60% relative humidity. A mortality count is made 48 hours after application of the test compound.

Compounds of formula I according to Example 1 exhibit good activity in this test.

EXAMPLE 9

Insecticidal Action (Systemic-Water): *Aphis Craccivora*

Pea seedlings which have been infested with aphids 24 hours before the start of the test are placed in 20 ml of an aqueous mixture containing 400 ppm of the test compound. The aqueous mixture is prepared from an emulsifiable concentrate or a wettable powder formulation of the respective test compound and is contained in a beaker sealed with a plastic lid in which holes have been punched. The root of each infested pea plant is pushed into the mixture through a hole in the plastic lid. The hole is then plugged with cotton wool in order to fix the plant in position and to protect it from contact with the gas phase of the mixture.

The test is carried out at 20° C. and 60% relative humidity. After 2 days the number of test insects no longer able to suck is evaluated in comparison with untreated controls in order to determine whether the test compound absorbed through the root kills the aphids on the upper parts of the plants.

Compounds of formula I according to Example 1 exhibit good systemic action against insects of the species *Aphis craccivora* in this test.

EXAMPLE 10

Stomach Toxicant Action and Contact Action Against *Laodelphax Striatellus* and *Nilaparvata Lugens* (Nymphs)

The test is carried out with growing plants. For this purpose 4 rice plants (thickness of the stem 8 mm) about 20 cm in height are planted into each of a number of pots (8 cm in diameter).

The plants are sprayed on a rotary table with 100 ml of an acetonic solution containing 400 ppm of the respective test compound. When the spray coating has dried, each plant is populated with 20 nymphs of the test organisms in the third stage. To prevent the cicadas from escaping, a glass cylinder open at both ends is slipped over each of the populated plants and covered with a gauze top. The nymphs are kept for 10 days on the treated plant until they have reached the next stage of development. A mortality count is made 1, 4 and 8 days after treatment.

Compounds of formula I according to Example 1 exhibit good activity in this test.

EXAMPLE 11

Systemic Action Against *Nilaparvata Lugens*

Rice plants which are about 10 days old and about 10 cm high are each placed in a plastic beaker containing 20 ml of an aqueous emulsion formulation of the test compound in a concentration of 400 ppm which is sealed with a plastic lid in which holes have been punched. The root of each rice plant is pushed through a hole in the plastic lid into the aqueous test formulation. The hole is then plugged with cotton wool in order to fix the plant in position and prevent any contact with the gas phase of the test formulation. The rice plant is then populated with 20 nymphs of *Nilaparvata lugens* in the $N_2$ to $N_3$ stage and covered with a plastic cylinder. The test is carried out at 20° C. and 60% relative humidity with a period of exposure of 16 hours per day. After 5 days the number of dead test insects is evaluated in comparison with untreated controls, thereby establishing whether the test compound absorbed through the roots kills the test organisms on the upper parts of the plants.

Compounds of formula I according to Example 1 exhibit good activity (mortality) against *Nilaparvata lugens* in this test.

EXAMPLE 12

Insecticidal Stomach Toxicant Action and Contact Action

Cotton plants about 25 cm high, in pots, are sprayed with aqueous emulsions containing the test compound in a concentration of 800 ppm.

When the spray coating has dried, the cotton plants are populated with *Spodoptera littoralis* and *Heliothis virescens* larvae in the $L_1$ stage. The test is carried out at 24° C. and about 60% relative humidity. After 120 hours a mortality count is made of the test insects in comparison with untreated controls.

Compounds of formula I according to Example 1 exhibit good activity (mortality) in this test.

EXAMPLE 13

Action Against *Nephotettix Cincticeps* (Nymphs)

The test is carried out with growing plants. For this purpose approximately 20-day-old rice plants about 15 cm in height are planted into pots (diameter 5.5 cm).

The plants are each sprayed on a rotary table with 100 ml of an acetonic solution containing 400 ppm of the test compound. When the spray coating has dried, each plant is populated with about 20 nymphs of the test organisms in the second or third stage. To prevent the cicadas from escaping, a plexiglass cylinder is slipped over each of the populated plants and covered with a gauze top. The nymphs are kept for 5 days on the treated plants, which have to be watered again at least once. The test is carried out at a temperature of about 23° C. at 55% relative humidity and with a period of exposure of 16 hours per day.

Compounds of formula I according to Example 1 exhibit good activity in this test.

What is claimed is:

1. A compound of formula I

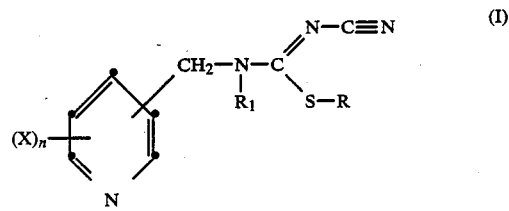

wherein R is $C_1$-$C_4$alkyl, cyclopropyl or benzyl; $R_1$ is $C_1$-$C_4$alkyl or cyclopropyl; X is halogen; and n is the integer 0, 1, 2 or 3.

2. A compound of formula I according to claim 1, wherein R is methyl, ethyl or benzyl; $R_1$ is methyl; X is chlorine; and n is the integer 0, 1 or 2.

3. A compound of formula I according to claim 2, wherein R and $R_1$ are methyl; and n is the integer 0.

4. A compound of formula I according to claim 1, wherein the pyridyl radical is a pyrid-3-yl or pyrid-4-yl radical.

5. A compound according to claim 4 of formula

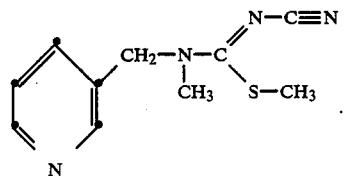

6. A composition for controlling insect pests and pests of the order Acarina, which comprises an effective amount of a compound of claim 1 together with an inert carrier.

7. A method according to claim 1 for controlling plant-destructive insects and representatives of the order Acarina.

8. A method according to claim 7 for controlling insect pests in rice crops.

9. A method of controlling destructive insects and representatives of the order Acarina, wherein the pests or their various stages of development or their loci are brought into contact with or treated with a pesticidally effective amount of a compound of formula I

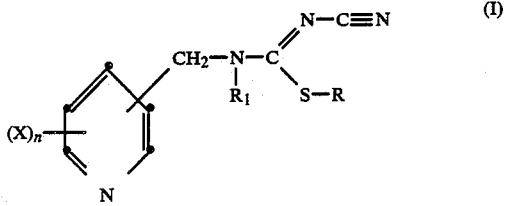

wherein R is $C_1$-$C_4$alkyl, cyclopropyl or benzyl, $R_1$ is $C_1$-$C_4$alkyl or cyclopropyl, X is halogen and n is 0, 1, 2 or 3.

10. The method of claim 9 wherein the pesticidally effective amount of the compound of formula I is in a composition which further comprises an inert carrier.

* * * * *